United States Patent [19]

Mullane, Jr.

[11] Patent Number: 4,741,877
[45] Date of Patent: May 3, 1988

[54] UNIFORMLY DEBOSSING AND APERTURING A MOVING PLASTIC WEB USING STATIONARY SUPPORT MEMBER IN FORMING AREA

[75] Inventor: William I. Mullane, Jr., Cincinnati, Ohio

[73] Assignee: The Procter & Gamble Company, Cincinnati, Ohio

[21] Appl. No.: 822,687

[22] Filed: Jan. 23, 1986

Related U.S. Application Data

[63] Continuation of Ser. No. 542,796, Oct. 17, 1983, abandoned.

[51] Int. Cl.⁴ .................... B29C 51/10; B29C 51/20
[52] U.S. Cl. ..................... 264/504; 264/555; 425/290; 425/326.1; 425/388
[58] Field of Search ............. 264/154, 156, 504, 555, 264/556; 425/290, 326.1, 387.1, 388

[56] References Cited

U.S. PATENT DOCUMENTS

| | | | |
|---|---|---|---|
| Re. 23,910 | 12/1954 | Smith et al. | 18/19 |
| 2,776,451 | 1/1957 | Chavannes | 18/10 |
| 3,054,148 | 9/1962 | Zimmerli | 18/56 |
| 3,932,248 | 1/1976 | Keaton | 425/388 |
| 3,954,368 | 5/1976 | Kawakami | 425/388 |
| 3,957,414 | 5/1976 | Bussey, Jr. et al. | 425/384 |
| 3,966,383 | 6/1976 | Bussey, Jr. et al. | 425/388 |
| 4,151,240 | 4/1979 | Lucas et al. | 264/504 |
| 4,155,693 | 5/1979 | Raley | 425/363 |
| 4,157,237 | 6/1979 | Raley | 425/363 |
| 4,226,828 | 10/1980 | Hall | 264/555 |
| 4,342,314 | 8/1982 | Radel et al. | 128/287 |
| 4,351,784 | 9/1982 | Thomas et al. | 264/22 |
| 4,364,723 | 12/1982 | Louis et al. | 425/388 |
| 4,541,794 | 9/1985 | Raley et al. | 425/388 |

FOREIGN PATENT DOCUMENTS

2021479  12/1979  United Kingdom .

Primary Examiner—Jan H. Silbaugh
Assistant Examiner—James Bartholomew
Attorney, Agent, or Firm—E. Kelly Linman; John V. Gorman; Richard C. Witte

[57] ABSTRACT

Method and apparatus for uniformly macroscopically expanding and, if desired, aperturing a plastic web. This is preferably accomplished by supporting the plastic web on a moving three-dimensional forming structure which is supported in a fluid pressure differential zone by a stationary support member. By providing a relationship between the size and pattern of the apertures in the stationary support member and the size and pattern of the apertures in the three-dimensional forming structure, substantially all of the apertures present in the forming structure are unobstructed by the stationary support member at some point during the forming structure's traverse of the fluid pressure differential zone. Thus the resultant plastic web is uniformly debossed and, if desired, apertured in the pattern of the three-dimensional forming structure.

4 Claims, 10 Drawing Sheets

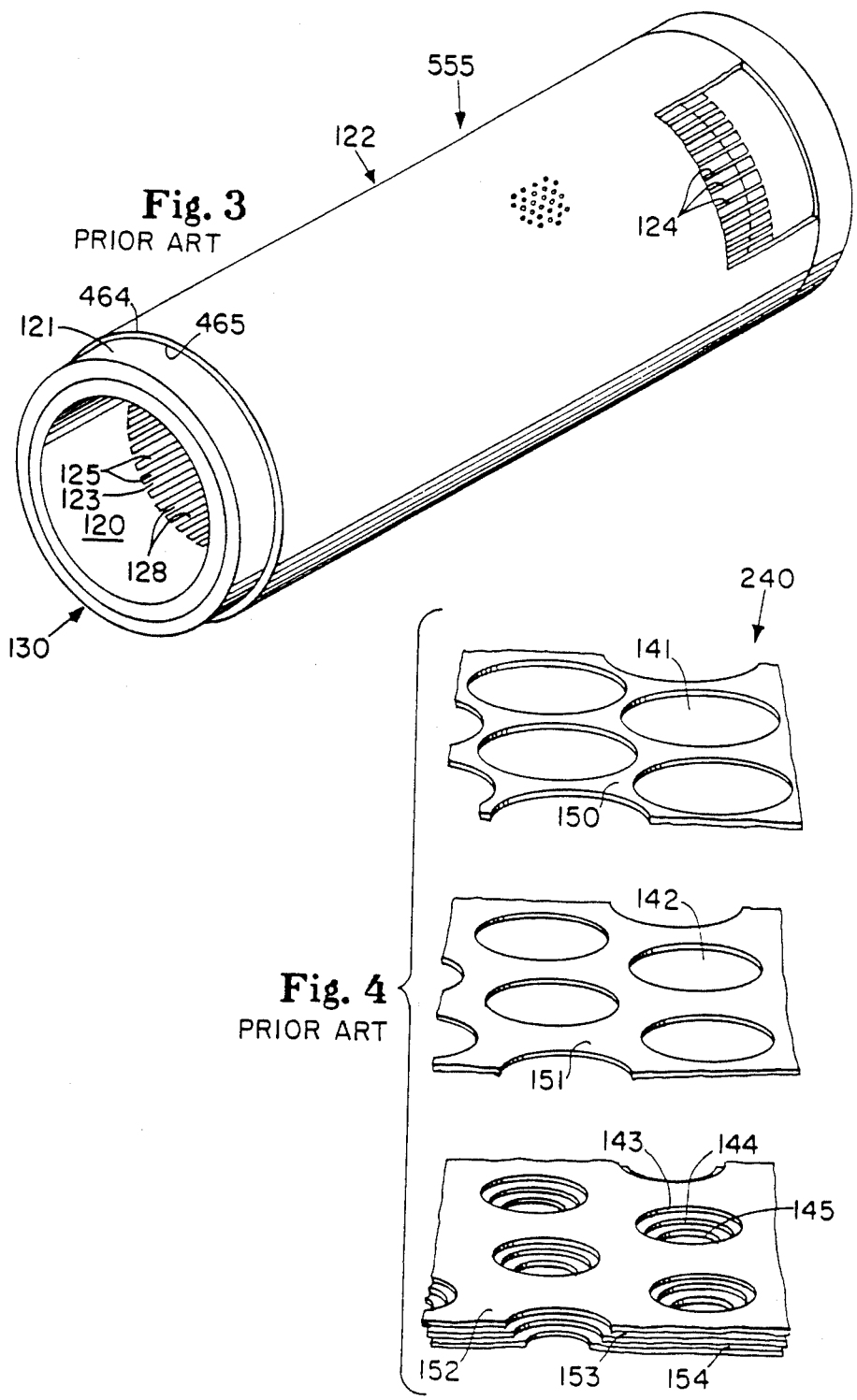

UNIFORMLY DEBOSSING AND APERTURING A MOVING PLASTIC WEB USING STATIONARY SUPPORT MEMBER IN FORMING AREA

This is a continuation of application Ser. No. 542,796, filed on Oct. 17, 1983, and now abandoned.

TECHNICAL FIELD

The present invention has relation to uniformly debossed and apertured, resilient plastic webs exhibiting fine-scale three-dimensional characteristics.

The present invention has further relation to method and apparatus for forming said plastic webs by supporting the moving three-dimensional forming structure on which said plastic webs are supported in a fluid pressure differential zone in such a manner that all portions of the web are exposed to said fluid pressure differential at some point during their traverse of the fluid pressure differential zone.

The present invention has further relation to method and apparatus for supporting the moving three-dimensional forming structure utilized to form said plastic webs as said structure passes over a fluid pressure differential zone so as to minimize the need for strength and rigidity in the forming structure per se, thereby greatly simplifying construction of the forming structure and extending its useful life.

The present invention has still further relation to method and apparatus for driving said three-dimensional forming structure across said fluid pressure differential zone in such a manner that torsional stresses experienced by the forming structure per se are minimized.

The present invention has still further relation to method and apparatus for continuously limiting to a predetermined maximum the force exerted between the lowermost surface of the moving, three-dimensional forming structure and the uppermost surface of the stationary support member as the forming structure traverses the fluid pressure differential zone, despite unexpected variations in processing conditions arising during the web forming operation.

BACKGROUND ART

Means for debossing and aperturing plastic webs are generally known in the art. U.S. Pat. No. 3,054,148 issued to Zimmerli on Sept. 18, 1962 discloses a process of producing a perforated thermoplastic sheet wherein a molding element rotates past a stationary drum having a fixed vacuum slot at a predetermined location on its periphery. The movable molding element is mounted around the surface of a stationary drum and is adapted to be rotated freely thereon. For purposes of rotating the molding element, a gear drive may be employed which is adapted to mesh with gearing provided on the element itself. As will be apparent from an inspection of the drawing figures in the Zimmerli patent, the aperture pattern in the molding element is relatively large, and the molding element illustrating in the drawing figures has sufficient rigidity and strength to permit its unsupported passage across a vacuum slot located at a predetermined point on the periphery of the stationary drum. Unfortunately, when fine-scale patterns involving three-dimensional plastic webs intended to provide the visual and tactile impression of fabrics are utilized, the forming structures necessary to produce such webs typically do not have sufficient rigidity or strength to permit their long term unsupported passage across a stationary vacuum slot. In addition, they often lack sufficient strength to permit long term transmission of the internal torsional stresses typically experienced when such forming structures are driven about a fixed drum at an elevated temperature.

Film forming methods and apparatus which appear to provide finer scale three-dimensional webs than those illustrated in the drawing figures of Zimmerli are also generally known in the prior art. For example, U.S. Pat. No. 2,776,451 issued to Chavannes on Jan. 8, 1957 discloses a moving perforate drum which passes across an internally located, fixed suction chamber secured at a predetermined point along the drum's periphery to impart a pattern to a heated thermoplastic film by the action of the suction. The forming structure layer(s) which contact the plastic material are preferably comprised of wire mesh. However, these forming structure layer(s) are supported about their entire periphery by means of a rigid perforate substrate which is fixed relative to the forming structure layer(s). Although the perforate substrate provides the necessary rigidity and strength to move the forming structure layer(s) across the fixed suction chamber, fluid flow through the forming structure layer(s) is limited to that provided by the pattern of perforations in the rigid substrate. Thus, the application of a uniform fluid pressure differential to the plastic web is not achieved and the resulting appearance of the processed plastic web is non-uniform.

Generally similar approaches are disclosed in U.S. Pat. Nos. 4,155,693 issued to Raley on May 22, 1979, 4,157,237 issued to Raley on June 5, 1979, 4,351,784 issued to Thomas et al. on Sept. 28, 1982 and British Patent Application No. GB 2,021,497A in the name of Raley and Adams, published on Dec. 5, 1979. All of the foregoing references disclose cylindrical drums used to pattern and/or perforate a heated plastic film subjected to vacuum while supported on the drum. All of said drums have a film forming surface exhibiting whatever three-dimensional pattern of perforations is desired. As with Chavannes, the film contacting surface of the drum, which acts as the forming structure, is supported by a rigid perforate substrate to permit the suction provided by an internally located, fixed vacuum chamber to act on the innermost surface of a plastic web as the drum and the web traverse the vacuum chamber. Hence, a problem inherent in the system disclosed by Chavannes is also present in the aforementioned systems. Because the rigid perforate substrate utilized to support the forming structure does not move relative to the forming structure, it impedes the application of a uniform fluid pressure differential across the surface of the plastic web supported at the periphery of the drum during the drum's passage across the vacuum chamber. Where particularly fine-scale three-dimensional patterns of perforations are involved, this may result in complete blockage of fluid flow through the forming structure at points where no perforations are present in the supporting substrate. As a result, there is a failure to uniformly impart the three-dimensional pattern exhibited by the forming structure to the plastic web.

U.S. Pat. No. Re. 23,910 issued to Smith et al. on Dec. 14, 1954 discloses a slightly different version of a fluid-pervious cylindrical drum utilized to impart a three-dimensional pattern to plastic webs subjected to suction while supported thereon. As with the aforementioned references, the drum employs a rigid perforate substrate. However, the drum of Smith et al. employs a multiplicity of support ribs secured at spaced locations about its periphery to provide support to a flexible foraminous forming structure. Unlike the drums disclosed in the aforementioned prior art patents to Raley and Thomas et al. and the British application of Raley et al., the drum's rigid perforate substrate, which rotates the foraminous forming structure across an internally located, fixed suction box, does not directly contact the innermost surface of the foraminous forming structure. However, the support ribs which do contact the innermost surface of the forming structure can impede or eliminate fluid flow through the forming structure at their points of contact and thereby create unpatterned and/or unapertured areas at the points of contact between the foraminous forming structure and the support ribs.

Other prior art approaches to debossing and aperturing plastic webs have employed flexible forming structures in lieu of rigidly constructed or rigidly supported cylindrical drums. In one embodiment for producing patterned plastic webs of predetermined length, the aforementioned patent to Smith et al. discloses the use of a discrete length of flexible foraminous forming material which passes across a stationary planar suction box with a web of plastic supported on its uppermost surface. The discrete length of foraminous material is rewound at the discharge end of the forming operation and repositioned at the infeed to produce another discrete length of film having the pattern of the foraminous material therein to avoid the effect of a seam. During its traverse of the suction box, the foraminous material is supported across the width of the plastic web by a multiplicity of support rollers extending in the cross-machine direction. The edges of the foraminous material are sealed to the suction box by means of movable deckle straps which travel with the foraminous material during its passage across the suction box. As can be seen in FIG. 1, the flexible foraminous material is not continuously supported in the machine direction intermediate the support rollers as it traverses the suction box. Accordingly, deformation of the flexible foraminous material can occur intermediate the support rollers due to the lack of continuous machine direction support. This problem become more pronounced where wider webs, more flexible foraminous materials and/or higher vacuum levels are involved. As will be appreciated, such deformation and wrinkling in the forming structure results in wrinkling and objectionable appearance in the resultant patterned plastic webs.

Other approaches employing flexible forming structures are disclosed in U.S. Pat. Nos. 3,957,414 issued to Bussey, Jr. et al. on May 18, 1976 and 3,966,383 issued to Bussey, Jr. et al. on June 29, 1976. However, the structure generally disclosed in the patents to Bussey, Jr. et al. utilizes a pair of support rollers in conjunction with fixed underlying deckles to impart a pattern to a plastic web which passes across a vacuum box at an elevated temperature. As can be seen from the drawing figures, the deckles utilized to seal the sides of the vacuum box also support the outermost edges of the flexible forming structure as it passes across the vacuum box, thereby blocking fluid flow through the forming structure at points coinciding with the deckles. Furthermore, for wider web widths, more flexible forming structures and/or higher vacuum levels, the use of such supporting deckles at points intermediate the outermost edges of the web would likely be necessary to provide support to the flexible forming structure in order to prevent deformation during its passage across the suction box. The use of such intermediate deckles would, of course, result in blockage of fluid flow at points coinciding with the deckles, and hence unpatterned and unapertured areas in the resultant plastic webs.

One particularly preferred prior art method for debossing and aperturing a running ribbon of thermoplastic film which substantially reduces the severity of the foregoing problem is generally disclosed in commonly assigned U.S. Pat. No. 4,151,240 issued to Lucas et al. on Apr. 24, 1979, and patent being hereby incorporated herein by reference. Briefly, the apparatus disclosed in the Lucas et al. patent comprises means for continuously converting a ribbon of thermoplastic film into a debossed and apertured film by directing hot air jets against one surface of the film while applying vacuum adjacent the opposite side of the film. The aforementioned operations are preferably carried out while maintaining sufficient control of the film to substantially obviate wrinkling and/or macroscopically distending the film. In a particularly preferred embodiment, the debossing and aperturing means include a rotatably mounted debossing/aperturing cylinder having closed ends, a nonrotating triplex vacuum manifold assembly and hot air jet means. The film contacting surface of the debossing/aperturing cylinder exhibits the three-dimensional pattern to be imparted to the plastic film.

In a particularly preferred embodiment of the Lucas et al. invention, the debossing/aperturing cylinder is constructed employing a tubular laminate forming structure of the type generally disclosed in commonly assigned U.S. Pat. No. 4,342,314 issued to Radel et al. on Aug. 3, 1982, said patent being hereby incorporated herein by reference. Forming structures of this type permit the production of debossed and apertured three-dimensional plastic webs having a predetermined, precisely regulated pattern of extremely fine scale. In particularly preferred embodiments, such webs can be made to appear fiber-like to the naked eye.

Unfortunately, when such finely patterned tubular forming structures are utilized on a cylindrical debossing/aperturing drum of the type generally disclosed in the aforementioned patent to Lucas et al., the radially oriented internal support members utilized to reinforce the tubular forming structure are likely to obstruct or totally block the fluid permeability of the forming structure at points of contact therebetween. Since there is no relative movement between the forming structure and the support members in use, the effectiveness of the fluid pressure differential, e.g., the vacuum, applied at the interior surface of said drum may be reduced or in some cases completely eliminated at such points of contact. Furthermore, the forming structure support members may actually contact and provide support to the film being processed, thereby tending to prevent rupture at such points. As a result, finely debossed and apertured films produced utilizing this technique typically remain unapertured wherever such a support member contacts the innermost surface of the tubular forming structure. This effect is most pronounced in situations where the overall thickness of the forming structure is relatively thin. As pointed out earlier herein, this is undesirable from both an aesthetic standpoint as well as from a functional standpoint in those situations where uniform fluid permeability is desired in the resultant three-dimensional plastic web.

The commonly assigned allowed patent application of William I. Mullane entitled METHOD AND APPA- RATUS FOR UNIFORMLY DEBOSSING AND APERTURING A RESILIENT PLASTIC WEB, Ser. No. 06/230,488, filed Feb. 2, 1981, issued on Apr. 10, 1984 as U.S. Pat. No. 4,441,952, and hereby incorporated herein by reference, discloses particularly preferred tubular forming structures constructed so as to alleviate the foregoing problems even further. In particular, such forming structure employ capillary networks which exhibit a cross-sectional area which reaches a minimum intermediate the outermost and innermost surfaces of the tubular forming structure and thereafter increases in the direction of the innermost surface of the forming structure to increase fluid permeability.

As with the structures of Radel et al., the tubular laminate forming structure of Mullane is preferably supported on a cylindrical drum of the type generally disclosed in the aforementioned patent to Lucas et al. by a multiplicity of radially oriented support members having lands which contact the innermost surface of the tubular member. Although the lands on the support members do not move relative to the innermost surface of the laminate forming structure, they are, in most instances, of insufficient cross-section to obstruct fluid flow through the capillary networks coinciding with their points of contact. Thus, the configuration of the individual capillary networks in the fluid-pervious laminate structure disclosed in the aforementioned patent application of Mullane permits substantially uniform application of a fluid pressure differential, usually vacuum, to the lowermost surface of the plastic material as the forming structure and the radially oriented support members traverse the vacuum chamber. In addition, the overall thickness of the Mullane structure prevents contact between the film and the support members prior to rupture. As a result, the heated plastic material is uniformly debossed and apertured substantially in conformance with the surface of the forming structure.

It will, of course, be appreciated by those skilled in the art that film forming structures of the type generally disclosed in the aforementioned application of Mullane are more complex, and hence more costly, than structures of the type generally disclosed in the aforementioned patents to Lucas et al. and Radel et al. Depending upon the useful life of such structures, this can significantly increase the cost of plastic webs produced thereon. It is further recognized that for webs involving extremely fine, closely spaced aperture patterns, even the invention disclosed in the aforementioned patent application of Mullane may not totally eliminate obstruction to fluid flow, since there is at least some contact between the innermost surface of the tubular forming structure and the radially oriented support members of the cylindrical drum.

Accordingly, it is an object of the present invention to provide method and apparatus for uniformly debossing and aperturing a resilient plastic web without limitation as to the fineness of scale of the aperture pattern exhibited by the forming structure.

It is another object of the present invention to provide method and apparatus for exposing the entire surface of a plastic web supported on a moving forming structure to a fluid pressure differential as the forming structure passes across a stationary fluid pressure differential zone.

It is another object of the present invention to provide means for driving said forming structure so that the torsional stress generated in said forming structure is minimized.

It is still a further object of the present invention to provide support means in the fluid pressure differential zone which are stationary relative to said traveling forming structure, yet which permit all portions of said forming structure to be subjected to a fluid pressure differential at some point during their traverse of said fluid pressure differential zone.

It is still another object of the present invention to provide support means which exert a constant force against the contacting surface of said forming structure as said forming structure passes across said fluid pressure differential zone, regardless of irregularities encountered during the processing operation.

It is still another object of the present invention to provide support means for said forming structure in said fluid pressure differential zone which will minimize wear and/or damage to the contacting surface of said forming structure and thereby greatly extend the life of said forming structure.

Yet another object of the present invention is to provide stationary support means in said fluid pressure differential zone which permit the use of either flexible or rigid forming structures.

DISCLOSURE OF THE PRESENT INVENTION

The present invention pertains, in a particularly preferred embodiment, to the provision of a three-dimensional resilient plastic web exhibiting a fine-scale uniformly apertured appearance throughout those areas where fluid permeability is desired, as well as to method and apparatus for producing such a web. The uniformity of aperturing is controlled by exposing the entire film forming structure on which the plastic material comprising the web is supported to a fluid pressure differential as said forming structure crosses a zone of three-dimensional expansion. While the fluid pressure applied to the web is normally in the form of vacuum applied to the lowermost surface of the forming structure, the present invention may be practiced with equal facility where other gases or liquids are directed at the outermost surface of the web to cause conformance of the web to the forming structure and ultimately rupture of the web at the points where it is unsupported by the forming structure. This may be done as an alternative to or in conjunction with the application of vacuum to the lowermost surface of the forming structure.

For purposes of clarity, the term "planar", when utilized herein to describe plastic webs, ribbons and films, refers to the overall condition of the web, ribbon or film when viewed by the naked eye on a macroscopic scale. In this context "planar" webs, ribbons and films may include webs, ribbons and films having fine scale surface aberrations on one or both sides, said surface aberrations not being readily visible to the naked eye when the perpendicular distance between the viewer's eye and the plane of the web is about 12 inches or greater.

By way of contrast, the term "macroscopically expanded", when used to describe three-dimensional plastic webs, ribbons and films, refer to webs, ribbons and films which have been caused to conform to the surface of a three-dimensional forming structure so that both surfaces thereof exhibit the three-dimensional pattern of said forming structure, said pattern being readily visible to the naked eye when the perpendicular distance between the viewer's eye and the plane of the web is about 12 inches.

Also, as used herein, the term "debossing" is generally employed when plastic webs, ribbons and films are caused to conform to a fluid-pervious three-dimensional forming structure by application of a fluid pressure differential. In the embodiments herein disclosed, the forming structure exhibits a pattern comprised primarily of female capillary networks into which the plastic is drawn or conveyed, i.e., points of debossment.

In a particularly preferred embodiment of the present invention, the film forming structure is supported by means of a fluid-pervious support member which is stationary relative to the moving forming structure as the forming structure traverses a fluid pressure differential zone, e.g., a vacuum slot. The fluid-pervious support member exhibits a pattern of openings across the surface of the vacuum slot which are so sized and shaped relative to the apertures in the forming structure that substantially all of the openings in the forming structure will be completely unobstructed and unsupported at some point during their traverse of the vacuum slot. Because substantially all of the apertures in the forming structure are thereby subjected to a fluid pressure differential at some point during their traverse of the vacuum slot, substantially all of the apertures in the forming structure are debossed and, if desired, apertured at those points where no support is provided by either the forming structure or the stationary support member.

In a particularly preferred embodiment, the forming structure comprises a cylindrical member which is provided with drive means at both ends to minimize internal torsional stresses normally experienced when the forming structure is rotated across the vacuum slot by driving only one end of the cylindrical member.

In yet another preferred embodiment of the present invention the stationary support member located in the vacuum slot exerts a constant force against the innermost surface of the forming structure during the latter's traverse of the vacuum slot. In a particularly preferred embodiment, this is accomplished by means of pneumatic or hydraulic cylinders operating at a predetermined pressure which is sufficient to support the forming structure in an undeformed condition during its traverse of the fluid pressure differential zone, but which is low enough to permit rapid movement and hence deflection of either the support member or the forming structure to avoid damaging the forming structure in the event an irregularity in processing conditions is suddenly experienced.

BRIEF DESCRIPTION OF THE DRAWINGS

While the specification concludes with claims particularly pointing out and distinctly claiming the present invention, it is believed that the present invention will be better understood from the following description in conjunction with the accompanying drawings in which:

FIG. 3 is an enlarged perspective view of the prior art debossing/aperturing cylinder shown in FIGS. 1 and 2;

FIG. 4 is an enlarged partially exploded segment of a prior art laminate film forming structure (shown prior to rolling and seaming);

DETAILED DESCRIPTION OF THE PRESENT INVENTION

Figure 1:
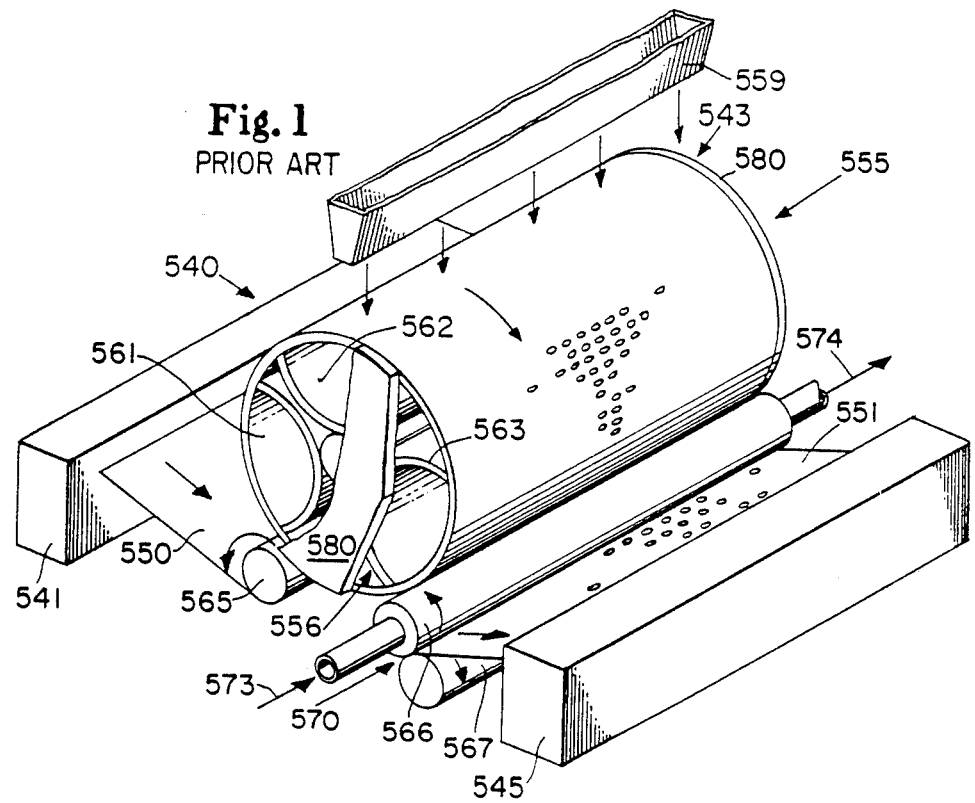
FIG. 1 is a simplified schematic illustration of prior art apparatus for debossing and aperturing a plastic film.

A prior art continuous film forming process employing a prior art tubular forming structure is schematically illustrated in FIG. 1. This process is generally described in commonly assigned U.S. Pat. No. 4,151,240 issued to Lucas et al. on Apr. 24, 1979, said patent being incorporated herein by reference. The apparatus 540 shown in FIG. 1 includes constant tension film supply means 541, debossing and aperturing means 543, and constant tension film forwarding and winding means 545. The frame, bearings, supports and the like which must necessarily be provided with respect to the functional members of apparatus 540 are not shown or described in detail.

Briefly, prior art apparatus 540, FIG. 1, comprises means for continuously converting a planar ribbon of thermoplastic film 550 into a three-dimensional debossed and apertured, i.e., perforated, film 551 by directing hot air jets against one surface of the film while applying vacuum adjacent the opposite surface of the film, and while maintaining sufficient control of the film to substantially obviate wrinkling and/or macroscopically distending the film. The apparatus 540 comprises means for maintaining constant machine direction tension in the film both upstream and downstream of a zone where the temperature is greater than the thermoplastic temperature of the film, but in which zone there is substantially zero machine direction and cross-machine direction tension tending to macroscopically distend the film. The aforementioned upstream and downstream tension controls and smooths the running ribbon of thermoplastic film. The zero tension zone results from the film in the zone being at a sufficiently high temperature to enable debossing and aperturing or aperturing it through the use of heated air and vacuum. The perforations shown in FIG. 1 are greatly enlarged to enable visually perceiving the nature of the difference between the imperforate planar film 550 and the resulting three-dimensional debossed and apertures film 551, as more fully described hereinafter.

As can be seen in FIG. 1, the prior art debossing and aperturing means 543 includes a rotatably mounted debossing/aperturing cylinder 555 having closed ends 580, a non-rotating triplex vacuum manifold assembly 556 and hot air jet means 559. The triplex vacuum manifold assembly 556 comprises three manifolds designated 561, 562 and 563. Also shown in FIG. 1 is a freely rotatable lead-on idler roll 565, a power rotated lead-off/chill roll 566, and a soft-faced (e.g., low density neoprene) roll 567 which is driven with the chill roll.

A thermoplastic ribbon of film running circumferentially about a portion of debossing/aperturing cylinder 555 is sequentially subjected to a first level of vacuum by manifold 561, a second level of vacuum by manifold 562, and a third level of vacuum by manifold 563. Vacuum applied to the film by manifold 561 maintains upstream tension in the film, vacuum applied by manifold 562 three-dimensionally debosses and perforates the film when hot air is directed radially inwardly against the film, and vacuum applied by manifold 563 cools the film to below its thermoplastic temperature and establishes downstream tension therein. The nip 570 intermediate chill roll 566 and the soft-faced roll 567 is nominally loaded to avoid ironing out the three-dimensional debossments which are formed in the film in the aforementioned manner. The passage of coolant through the chill roll, as indicated by arrows 573, 574 in FIG. 1, enables the apparatus to handle thicker films or to be operated at higher speeds.

Referring again to FIG. 1, the constant tension film supply means 541 and the constant tension film forwarding and winding means 545 are substantially identical to and function substantially identically to the corresponding portions of the apparatus shown and described in commonly assigned U.S. Pat. No. 3,674,221 issued to Reimersma on July 4, 1972 and hereby incorporated herein by reference. The debossing and aperturing means 543 comprises the rotatably mounted debossing/aperturing cylinder 555, means (not shown) for rotating the cylinder 555 at a controlled peripheral velocity, the non-rotating triplex vacuum manifold assembly 556 inside the debossing/aperturing cylinder 555, means (not shown) for applying controlled levels of vacuum inside the three vacuum manifolds 561, 562, and 563 comprising the triplex manifold assembly 556, and hot air jet means 559.

Figure 2:
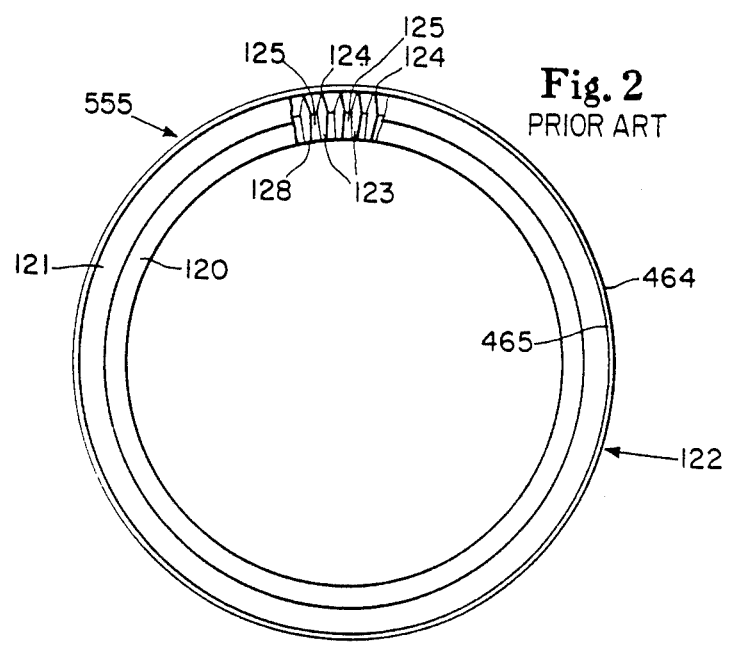
FIG. 2 is an enlarged end view of the prior art debossing/aperturing cylinder shown in FIG. 1.

The debossing/aperturing cylinder 555 shown in FIG. 1 is illustrated in greater detail in FIGS. 2 and 3. The cylinder 555 comprises a cage 120, a support ring 121 and a relatively thin walled film-contacting tubular member 122 which serves as the film forming structure. The cage 120 comprises a multiplicity of circumferentially spaced, radially oriented, longitudinally extending bars 123 which are tapered to relatively small, radially outwardly facing lands 124. The spaced bars 123 have vacuum communicating passageways 125 provided therebetween. The bars 123 also have radially inwardly facing lands 128 which corporately provide a cylindrical vacuum sealing surface against which the vacuum seals associated with the triplex vacuum manifold 556 are biased. Thus, as the prior art debossing/aperturing cylinder 555 rotates, its vacuum sealing surface slides over the seals (not shown) of the non-rotating triplex vacuum manifold assembly 556.

At least one end 130, FIG. 3, of the debossing/aperturing cylinder 555 is open in order to provide easy insertion/removal of the triplex vacuum manifold assembly 556. Therefore, in order to rotatably support the open end 130 of cylinder 555, it is provided with a bearing-race support ring 121, as shown in FIGS. 2 and 3, which rides on bearings (not shown) which are appropriately secured to the apparatus frame, e.g., fixed end wall 580.

The tubular member 122, which functions as the film forming structure, is constructed by generally following the teachings of the aforementioned commonly assigned U.S. Pat. No. 4,342,314 issued to Radel et al. on Aug. 3, 1982. Tubular member 122 is fluid pervious and comprises a relatively thin laminate structure such as 240, a partially exploded planar segment of which is shown in FIG. 4, in contacting relation with the small lands 124 of the radially oriented, longitudinally extending support bars 123 of cage 120. The lands 124 are small and the tubular member 122 is relatively thin-walled because the apparatus 540, FIG. 1, is configured to deboss and aperture an extremely fine three-dimensional pattern of tapered capillaries into a relatively thin thermoplastic film such as low density polyethylene film.

Only the outermost surface 464 of prior art tubular forming member 122 contacts the plastic web brought in contact therewith. The innermost surface 465 of tubular member 122 contacts the lands 124 of prior art support members 123 during the debossing/aperturing operation.

In the illustrated embodiment, prior art tubular member 122 is constructed generally in accordance with the teachings of the aforementioned patent to Radel et al. utilizing a stack of copper plated, photoetched metallic laminae exhibiting concentrically aligned patterns of apertures, said laminae being bonded to one another at contact points while subjected to heat and pressure. The resultant laminate structure is thereafter rolled into a tubular shape and its free edges are bonded to one another to form a continuous tubular forming structure, all generally in accordance with the teachings of the aforementioned patent to Radel et al.

FIG. 4 discloses a particular prior art laminate structure 240 utilized to produce a fluid-pervious plastic web exhibiting a fine scale pattern of tapered capillaries, as generally illustrated and described in commonly assigned U.S. Pat. No. 3,929,135 issued to Thompson on Dec. 30, 1975 and hereby incorporated herein by reference. The laminate structure 240 (shown prior to rolling and seaming) is comprised of a stack of individual laminae 150, 151, 152, 153 and 154. Each lamina has a pattern of regularly spaced openings or apertures therein. In the illustrated embodiment, the pattern of openings 141 in lamina 150 is concentrically aligned with the pattern of openings 142 in lamina 151, the pattern of openings 143 in lamina 152, the pattern of openings 144 in lamina 153 and the pattern of openings 145 in lamina 154. Thus, the apertures in successive lamina coincide with one another. The diameter of openings 141 is greater than the diameter of openings 142 which in turn, is greater than the diameter of openings 143, etc., all the way through laminae 153 and 154. The resultant laminate structure 240 provides a regulated pattern of substantially conically-shaped openings extending from the uppermost lamina 150 to the lowermost lamina 154.

Figure 5:
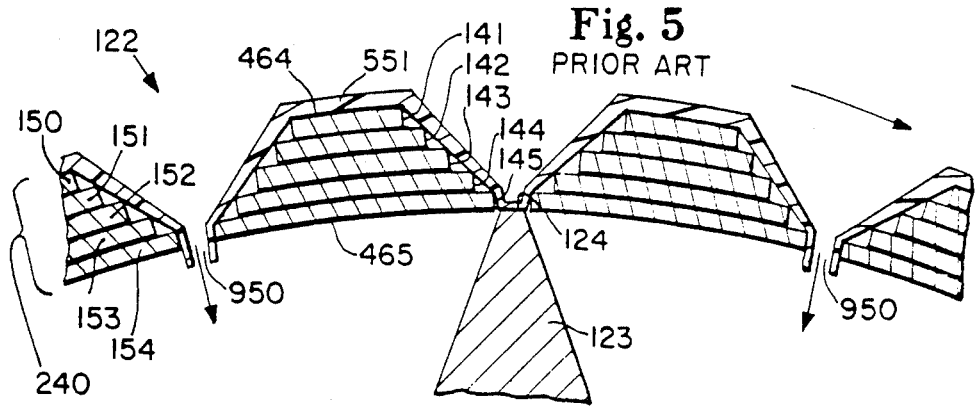
FIG. 5 is an enlarged, simplified cross-sectional segment of a prior art tubular forming structure formed from a laminate of the type generally shown in FIG. 4 installed on a prior art cylindrical cage of the type generally shown in FIGS. 1-3.
Figure 6:
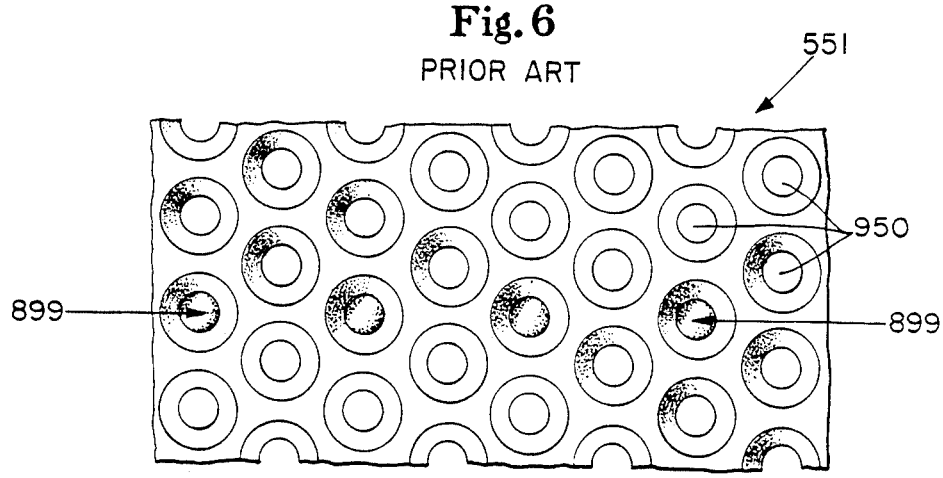
FIG. 6 is a plan view enlarged many times actual size of a prior art plastic film which has been debossed and apertured on a prior art structure exhibiting an aperture pattern of the type generally shown in FIG. 5.

FIG. 5 is a greatly enlarged, simplified cross-sectional view of a segment of a prior art tubular member 122 installed on a prior art cylindrical cage 120 of the type shown in FIGS. 1–3, said tubular member being comprised of a tubular shaped, rolled and seamed laminate structure 240 of the type generally shown in FIG. 4. FIG. 5 is taken during the web processing operation through a partially obstructed, conically-shaped capillary network created in laminate forming structure 240 by the concentrically aligned holes in each lamina. As shown in FIG. 5, the width of land 124 of prior art support member 123 is such that it partially obstructs cylindrical opening 145 in lowermost lamina 154 of the laminate structure 240. As a result, when the plastic web is subjected to heat, in this case hot air blast 559, and vacuum is applied to the interior surface of debossing-/aperturing cylinder 555, the initially planar plastic film is caused to conform approximately to the tapered capillary networks generally illustrated in FIG. 5. However, as the film draws nearer the innermost surface 465 of tubular member 122, it contacts land 124 of support member 123. Thus, although the film is thinned due to its being forced to conform to the conically-shaped capillary network in the laminate structure 240, it is not perforated at this particular point due to the partial obstruction of air flow as well as the structural support provided to the film by land 124 on support member 123 during processing. By way of contrast, the adjacent capillary networks in the laminate structure are unobstructed. Consequently, the film is both debossed and apertured at the unobstructed locations, as generally shown in FIGS. 5 and 6 to form apertures 950 in the macroscopically expanded, three-dimensional film 551. Because there is no relative movement between support members 123 and laminate structure 240 as debossing-/aperturing cylinder 555 traverses vacuum manifold 562, the unapertured condition illustrated in FIG. 5 remains when the macroscopically expanded, three-dimensional film 551 is removed from the debossing/aperturing cylinder.

Since the radially oriented support members 123 extend generally parallel to the cylinder's axis of rotation, the macroscopic effect of the obstruction illustrated in FIG. 5 is a continuous line of debossed, but imperforate film extending throughout the areas where prior art support members 123 contact the innermost surface 465 of prior art tubular forming member 122, thereby partially obstructing apertures 145 in lamina 154. The areas of contact between the film and support members 123 are clearly apparent from FIG. 6 (see arrows 899) which is a plan view illustration of a macroscopically expanded, three-dimensional plastic web 551 which has been subjected to a fluid pressure differential while supported on a forming structure exhibiting a pattern of tapered capillaries of the type generally illustrated in FIG. 5 to form a multiplicity of apertures 950. Since a multiplicity of prior art support members 123 is normally required to impart sufficient strength and mechanical support to prior art tubular member 122 across the width of the cylinder 555 about its entire periphery, a corresponding multiplicity of imperforate areas results in the film. While in the illustrated prior art embodiment, these imperforate areas extend in a direction generally parallel to the cylinder's axis of rotation, it will be appreciated that the particular configuration and orientation of any imperforate areas exhibited by the web will be dependent upon the configuration and orientation of the particular support members employed to mechanically reinforce tubular member 122 as well as the degree of obstruction caused by the support members. In this regard it will be recognized that where extremely fine patterns of apertures are employed in prior art tubular member 122, complete blockage of the apertures may result. This can result in the coinciding portions of the web being neither debossed nor perforated.

It is, of course, recognized that not all prior art three-dimensional apertured webs, whether processed from rolls of planar plastic film or extruded as a melt directly onto the surface of a three-dimensional forming structure, exhibit the imperforate characteristic described in the preceding paragraph. Where the apertures are large in relation to the area of obstruction created by land areas 124 of support members 123, the obstruction to fluid flow may prove insignificant. Complete aperturing may occur despite the presence of the obstruction, provided the overall thickness of the forming structure is sufficient to permit rupturing of the film before it can contact the land areas 124 of support members 123.

Figure 7:
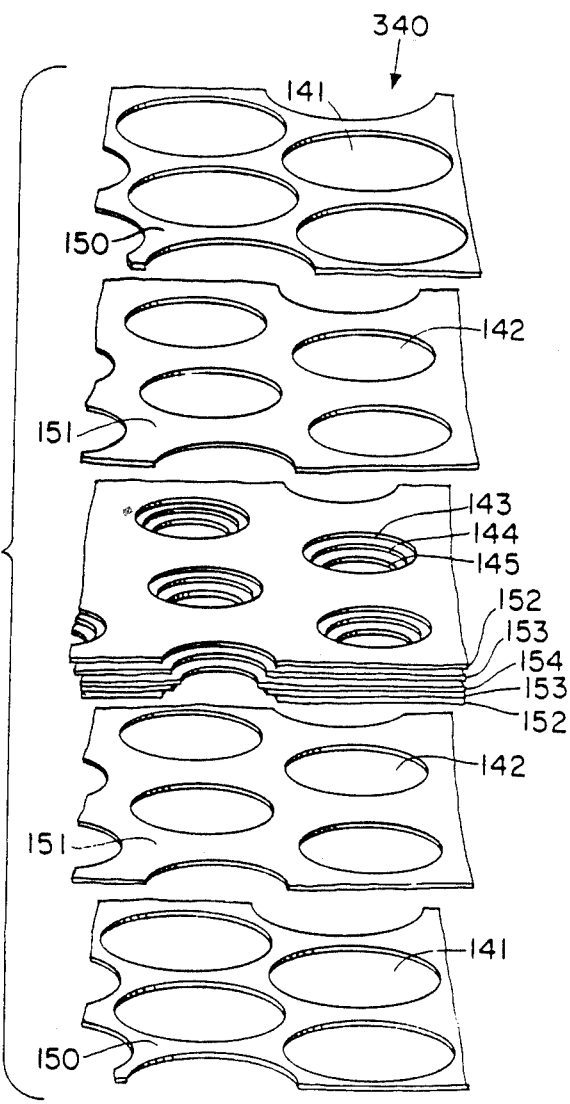
FIG. 7 is an enlarged, partially exploded segment of another laminate forming structure (shown prior to rolling and seaming)

One preferred means of minimizing the incomplete debossing and/or aperturing problem in those situations where land areas 124 of support members 123 either significantly reduce the fluid permeability of the forming structure and/or contact and support the film being processed thereon prior to rupture is disclosed in the commonly assigned, allowed patent application of William I. Mullane entitled "METHOD AND APPARATUS FOR UNIFORMLY DEBOSSING AND APERTURING A RESILIENT PLASTIC WEB, Ser. No. 230,488, filed Feb. 2, 1981 and issued on Apr. 10, 1984 as U.S. Pat. No. 4,441,952, said patent application being incorporated herein by reference. FIG. 7 is an illustration generally similar to that of FIG. 4, but showing a laminate forming structure 340 of the type generally disclosed in the aforementioned patent application of Mullane (shown prior to rolling and seaming). The forming structure of FIG. 7 differs from that illustrated in FIG. 4 in that the number of laminae has been increased to totally eliminate the support provided to the film by lands 124 on longitudinally extending support members 123. In addition, the order in which the laminae are stacked has been modified to maximize air flow during the film perforating operation. In the disclosed embodiment, another set of laminae 153, 152, 151, and 150 has been added to the lowermost surface of lamina 154. However, the added laminae are stacked in reverse order, as generally shown in FIG. 7, so that the resultant capillary networks connecting the outermost and innermost surfaces of prior art tubular forming member 122', FIG. 8, first converge to a minimum cross-sectional area at lamina 54 and then diverge to their original cross-sectional area intermediate the outermost and the innermost surfaces of the tubular member.

Figure 8:
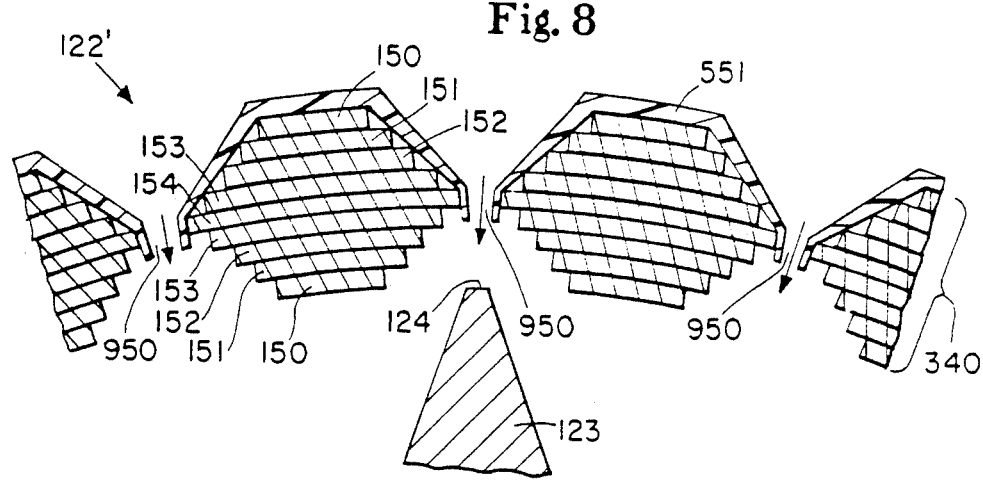
FIG. 8 is an enlarged, simplified cross-sectional segment of a tubular forming structure formed from a laminate of the type generally shown in FIG. 7 applied to a prior art cylindrical cage of the type generally shown in FIGS. 1-3.

The practical effect of this structural difference is illustrated in simplified form in FIG. 8. Because the overall thickness of tubular forming member 122' is greater than that of prior art tubular forming member 122, the land areas 124 of longitudinally extending support members 123 are far enough removed from the surface of the plastic film being debossed and apertured that the film does not contact the support members during the perforating operation. Furthermore, because the lands 124 are considerably smaller in width than the diameter of the cylindrical apertures 141 in lamina 150 adjacent thereto, fluid flow, in this case hot air, is not obstructed at the centrally located cylindrical openings 145 in lamina 154. As a result, the plastic film is drawn down into the cylindrical openings 145 contained in lamina 154. Due to the lack of support, the film ruptures to form a uniform pattern of apertures 950 in the macroscopically expanded, three-dimensional web 551, as generally shown in FIG. 8.

Due to the added complexity, tubular forming structures such as 122' illustrated in FIG. 8 are more expensive to manufacture than prior art tubular forming structure such as 122 illustrated in FIG. 5.

Figure 9:
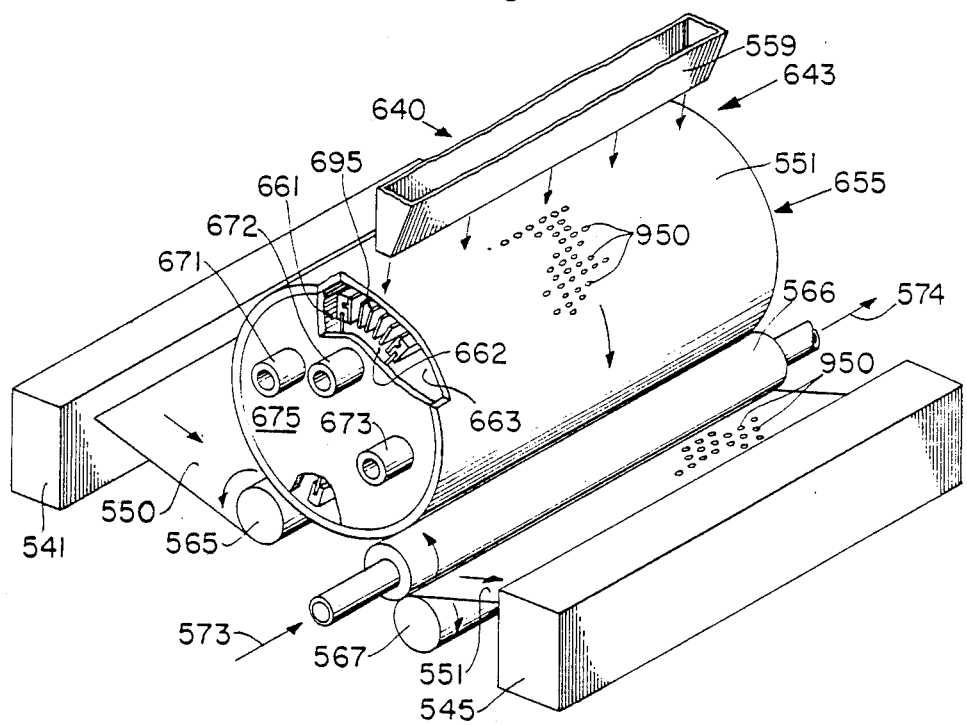
FIG. 9 is a simplified schematic illustration of preferred apparatus for uniformly debossing and, if desired, aperturing a web of substantially planar plastic film generally in accordance with the present invention.

Accordingly, the present invention addresses an alternative approach to solving the incomplete debossing and/or aperturing problem. FIG. 9 is a simplified schematic illustration of particularly preferred apparatus for uniformly debossing and aperturing a plastic film generally in accordance with the present invention.

Briefly, apparatus 640 is, in general, similar to prior art apparatus 540 shown in FIG. 1. For clarity, similar elements of apparatus 640 have been identified utilizing the same reference numeral utilized to describe apparatus 540. As with prior art apparatus 540, apparatus 640 comprises means for continuously converting a planar ribbon of thermoplastic film 550 into a three-dimensional debossed and apertured or apertured web 551 by directing hot air jets against one surface of the film while applying vacuum adjacent the opposite surface of the film, and while maintaining sufficient control of the film to substantially obviate wrinkling and/or macroscopically distending the film. The chief difference between prior art apparatus 540 and apparatus 640 of the present invention centers around debossing and aperturing means 643, which includes a rotatably mounted debossing/aperturing cylinder 655. The details of construction of debossing/aperturing means 643 will be described in greater detail hereinafter, particularly with respect to the differences in construction from prior art debossing/aperturing means 543 generally shown in FIG. 1.

Figure 10:
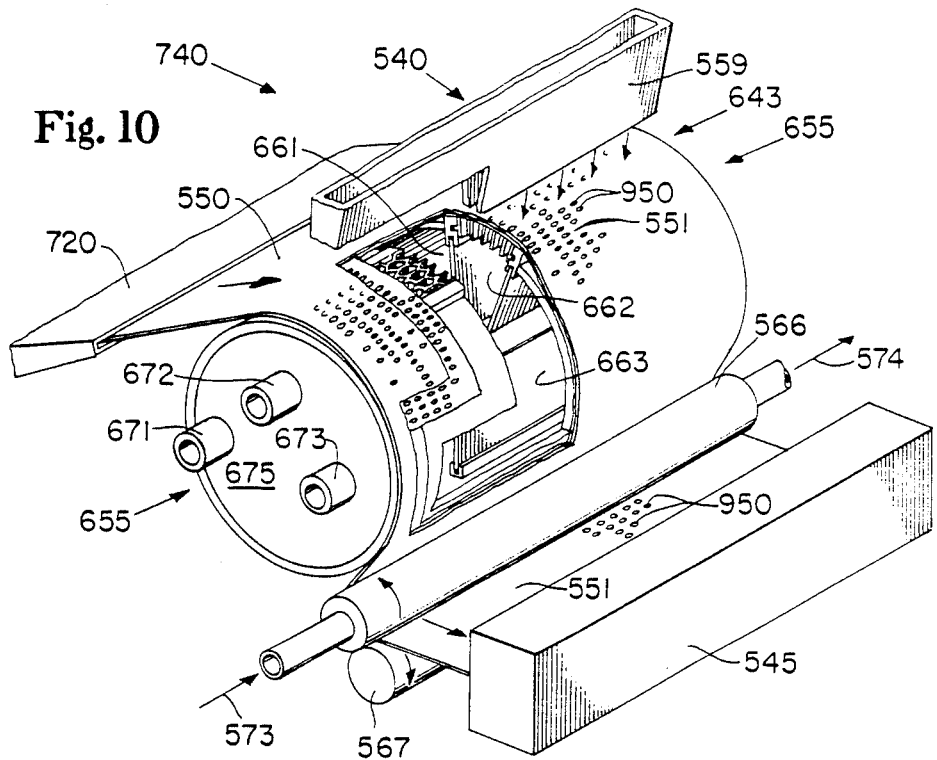
FIG. 10 is a simplified schematic illustration of preferred apparatus for forming a macroscopically expanded, and, if desired, uniformly apertures, three-dimensional plastic web by direct extrusion generally in accordance with the present invention.

FIG. 10 is a view generally similar to FIG. 9, but showing an alternative forming process wherein a layer of heated plastic material is extruded directly from an extruder nozzle 720 directly onto the periphery of a debossing/aperturing cylinder 655. With the possible exception of the temperature of the plastic material comprising film 550 at its point of contact with debossing/aperturing cylinder 655, the processing operation hereinafter described in detail is generally similar for the process embodiments shown in both FIGS. 9 and 10.

Figure 11:
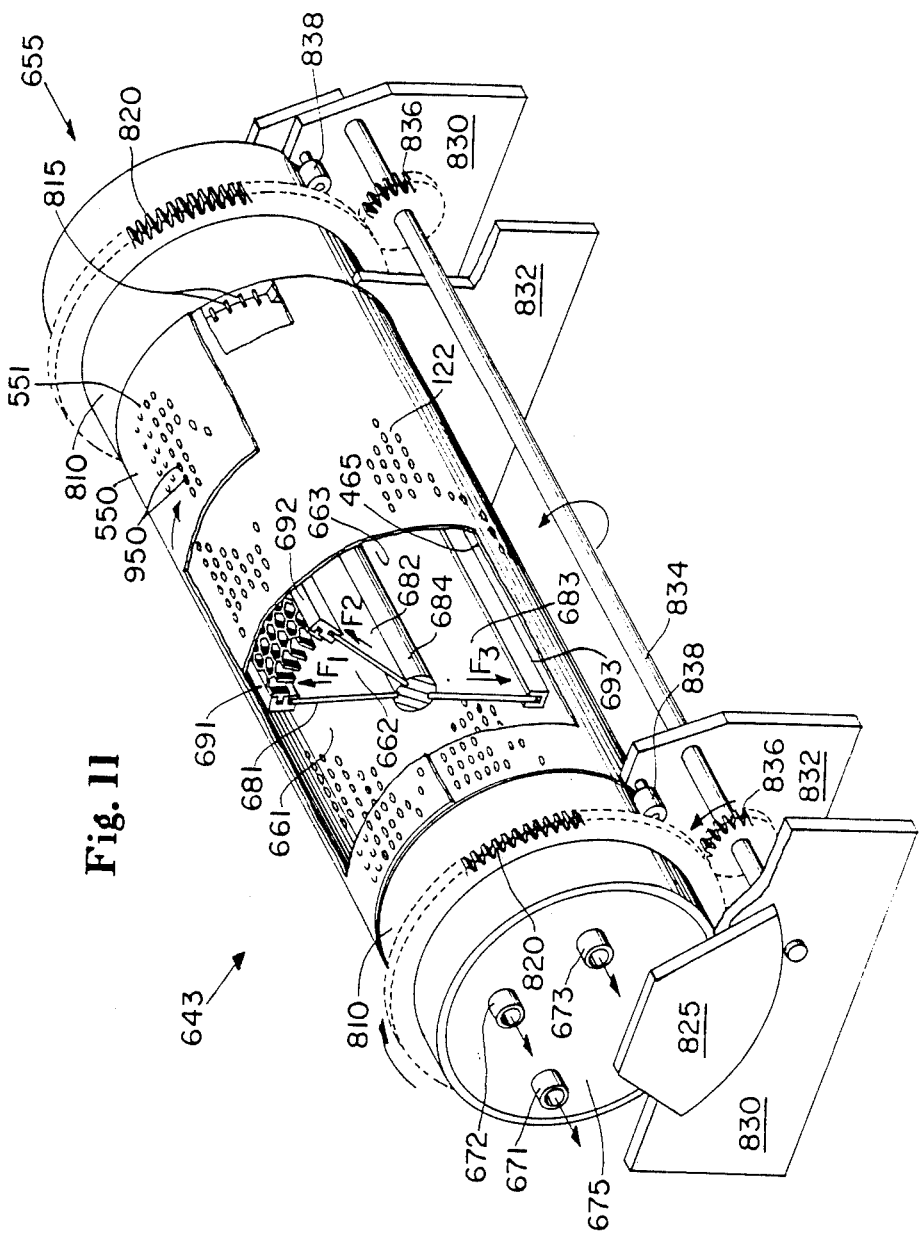
FIG. 11 is an enlarged perspective view of a debossing/aperturing cylinder of the type generally shown in FIGS. 9 and 10.

An enlarged simplified schematic illustration of debossing/aperturing means 643 used in the process embodiments of FIGS. 9 and 10 is generally disclosed in FIG. 11. Debossing/perforating cylinder 655 comprises a prior art laminate tubular member 122 of the type generally disclosed in FIG. 5. However, there are no prior art support members 123 present in cylinder 655. Rather, the outermost edges of tubular member 122 are secured by any suitable means, such as drive pins 815, to a pair of bearing races 810 located at each end of the tubular member. Each bearing race 810 is provided with a gear 820 which extends continuously about its periphery. The bearing races 810 are cradled and supported by means of a multiplicity of bearing rollers 838 which are rotatably mounted in support members 830, 832. Cylinder 655 is constrained from substantial movement in a direction parallel to its axis of rotation by means of a pair of thrust plates 825, said thrust plates being releasably secured to the outermost surface of each support member 830, as generally shown in FIG. 11.

Cylinder 655 is preferably driven by any suitable drive means (not shown) which rotates shaft 834, and consequently gears 836 secured to shaft 834, in a counterclockwise direction. Gears 836 engage gears 820 on bearing races 810, thereby driving cylinder 655 in a clockwise direction. Due to the extremely fine detail present in tubular member 122, its mechanical strength, and hence its ability to withstand high stresses for prolonged periods, is often quite limited. Because cylinder 655 is driven from both ends, the internal torsional stresses normally experienced when tubular member 122 is driven from only one end are essentially eliminated. As will be appreciated, minimizing the amount of in use torsional stress experienced by tubular forming member 122 normally serves to substantially extend its useful life.

As can be seen in FIG. 11, the interior portions of debossing/aperturing cylinder 655 are preferably separated into three chambers 661, 662 and 663 by means of substantially rigid radially extending walls 681, 682 and 683 respectively. The innermost edges of walls 681, 682 and 683 are fixedly secured to one another along the axis of rotation of drum 655. The outermost edge of each of said walls is provided with a radially movable wear strip, i.e., 691, 692 and 693. Each wear strip is preferably subjected to a radially outwardly extending force which, in turn, is exerted against the innermost surface 465 of tubular forming member 122. The wear strips provide sliding seals against the innermost surface 465 of tubular member 122. In a particularly preferred embodiment, the force $F_1$ exerted against wear strip 691, the force $F_2$ exerted against wear strip 692 and the force $F_3$ exerted against wear strip 693 are substantially equal to one another, and are provided by means of radially extending hydraulic or pneumatic cylinders (not shown) which are hydraulically or pneumatically interconnected to one another and controlled by means of a common pressure regulator. Radially extending walls 681, 682 and 683 are secured at opposite ends to a closure member 675 which is, in turn, secured to a support member 825. This prevents rotation of the radially extending walls when cylinder 655 is rotated. As generally shown in FIG. 11, stationary end closure members 675 maintain a sealed engagement against the innermost surfaces of rotatably mounted bearing races 820.

To minimize wear due to friction between the innermost surface 465 of tubular forming structure 122 and support member 695, including supporting wear strips 692 and 693, the wear strips and support member can be fabricated from low friction materials such as molded plastic, teflon, nylon, etc. Since they can be easily replaced, they can be fabricated from a material which is softer than the innermost surface 465 of tubular member 122. Thus, most of the frictional wear will be confined to these softer, easily replaceable elements, thereby extending the useful life of the three-dimensional forming structure, which is typically much higher in cost. Other exemplary means of reducing frictional wear of the innermost surface 465 of tubular member 122 include hardening of the surface 465 and, in a particularly preferred embodiment, lubricating the wear strips 692 and 693 at their points of contact with innermost surface 465 by injection of a pressurized fluid such as water at said points of contact.

As with the prior art embodiment 543 shown generally in FIG. 1, the arrangement disclosed in FIG. 11 permits maintenance of three separate vacuum levels in chambers 661, 662 and 663. This may be achieved by connecting a suitable source of vacuum to each of the chambers via conduits 671, 672 and 673, respectively. In this regard it should be noted, that while the tension isolation provided to the film by vacuum chambers 661 and 663 is in many instances desirable, it is not critical to the practice of the present invention. For example, in the direct extrusion embodiment of FIG. 10 the extruded resin comprising film 550 is preferably applied directly at the leading edge of the fluid pressure differential zone, i.e., vacuum chamber 662, thus by passing vacuum chamber 661 altogether. Thus, it will be appreciated that only a single fluid pressure differential zone, e.g., vacuum chamber 662, is required to uniformly deboss and, if desired, uniformly aperture a plastic web in accordance with the process herein described.

Figure 12:
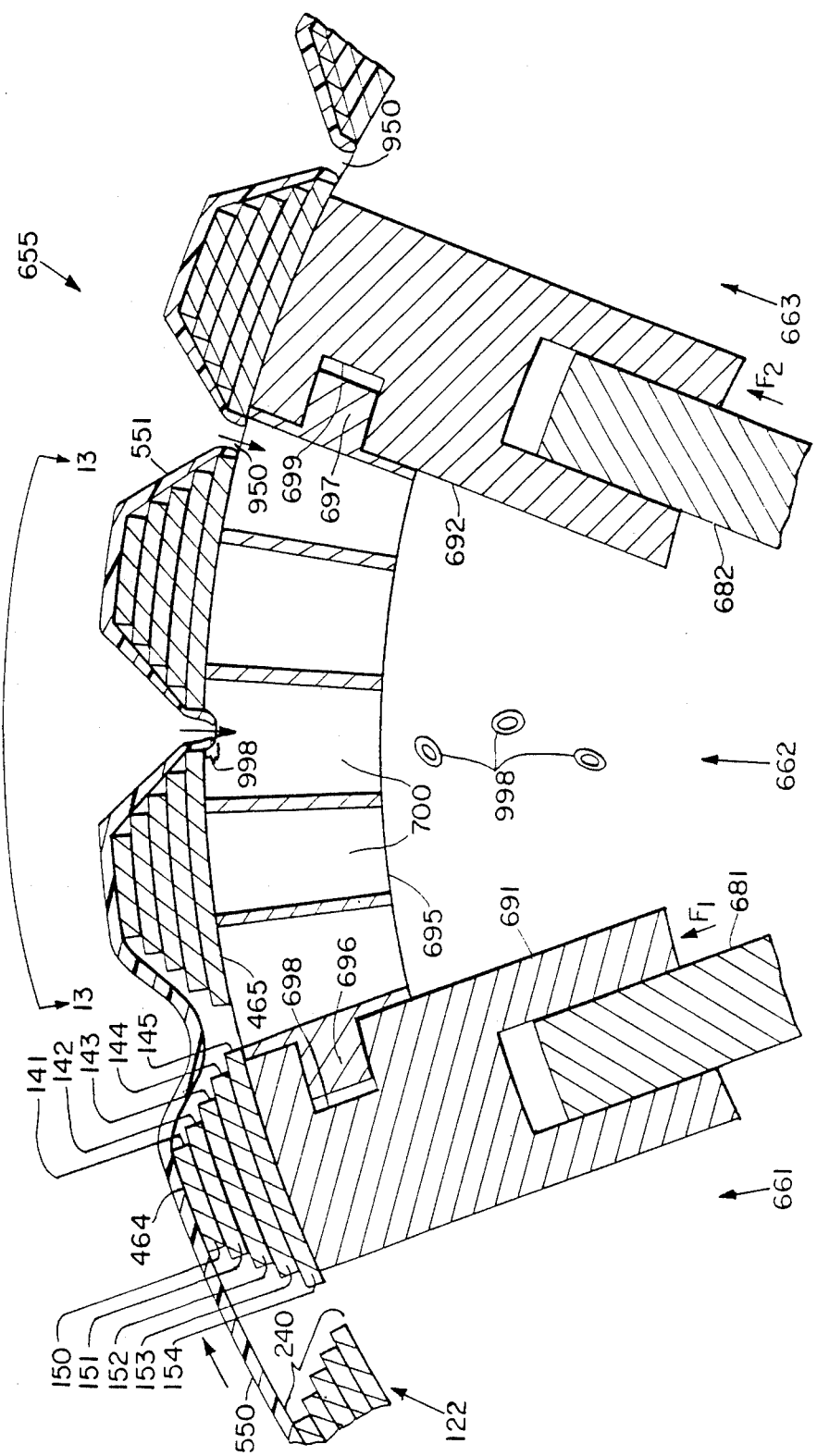
FIG. 12 is an enlarged, simplified cross-sectional segment of a tubular forming structure of the type generally shown in FIGS. 4 and 5 passing across a peripherally stationary support member located in a fixed vacuum slot of the type generally shown in FIGS. 9, 10 and 11.

FIG. 12 is a greatly enlarged cross-section taken through vacuum chamber 662 along section line 12—12 of FIG. 11. As can be seen in FIG. 12, wear strips 691 and 692 are in sliding engagement with radially extending walls 681 and 682, respectively. As can also be seen in FIG. 12, wear strips 691 and 692 are provided with arcuate grooves 698 and 699 in order to engage arcuate projections 696 and 697, respectively, of support member 695.

Figure 13:
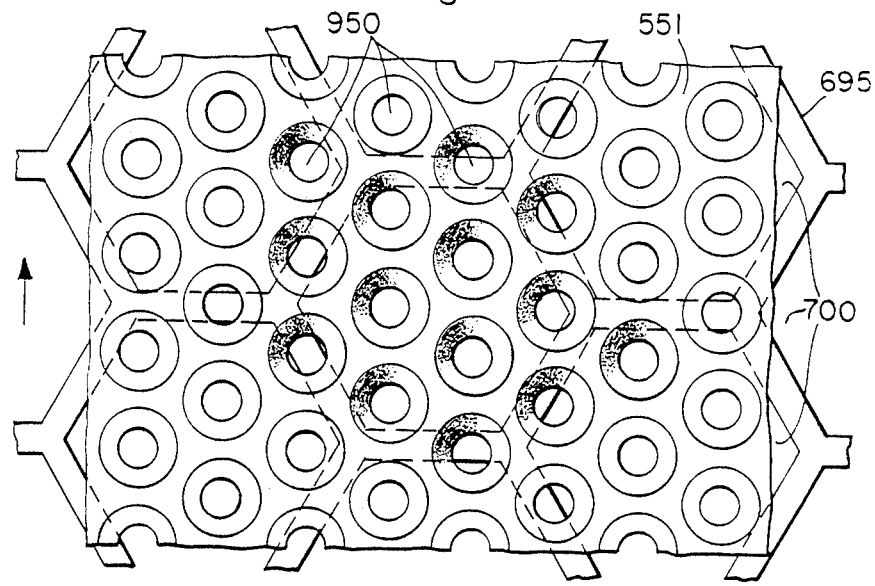
FIG. 13 is a greatly enlarged view taken at a point corresponding to view line 13—13 of FIG. 12, said view showing a preferred size and spacing relationship between the apertures in the stationary support member and the apertures in the moving forming structure (shown on a different relative scale than in FIG. 12 for purposes of clarity) at one point during the forming structure's traverse of the vacuum slot.

In the embodiment shown in FIG. 12, support member 695 comprises a substantially rigid honeycomb structure having hexagonally-shaped apertures or openings 700, as generally shown in the greatly enlarged view of FIG. 13. (Note that in FIG. 13 the size and spacing of openings 700 in support member 695 relative to the size and spacing of apertures 950 in web 551 have been altered from those shown in FIG. 12 for purposes of clarity.) As can be seen in FIGS. 10, 11 and 12, support member 695 extends substantially all the way across vacuum chamber 662 in both the machine and cross-machine directions, thereby providing continuous machine direction and cross-machine direction support to tubular forming member 122 during its traverse of the fluid pressure differential zone. The hexagonally shaped openings 700 are so sized and oriented that every aperture 145 in lamina 154 of laminate forming structure 240 will at some point in its traverse of peripherally stationary support member 695 be fully exposed to the fluid pressure differential, i.e., the hexagonally-shaped apertures or openings 700 in support member 695 overlap one another in the cross-machine direction so that a continuous, uninterrupted straight line oriented parallel to the machine direction and completely traversing the fluid pressure differential zone cannot be inscribed on the land area defining the hexagonally-shaped openings in the support member 695. This is best illustrated in FIG. 13. As a result, the fluid pressure differential, in this case the heated air from nozzle 559 and suction imposed by vacuum chamber 662, conforms the initially planar heated plastic material comprising film 550 to the tubular forming member 122 along its entire surface. Because all of the capillary networks in the laminate forming structure 240 comprising tubular member 122 are fully exposed to the fluid pressure differential at some point during their traverse of vacuum chamber 662, a multiplicity of apertures 950 is created in the plastic web, each of said apertures corresponding to one of the apertures 145 in lamina 154 of the laminate forming structure.

In the embodiment illustrated in FIG. 12, an annular ring 998 of the plastic material comprising macroscopically expanded three-dimensional web 551 projects slightly below the innermost surface 465 of the tubular forming member 122 once rupture occurs. Because the entire surface of tubular forming member 122 is exposed to the fluid pressure differential present at vacuum chamber 662 at some point during its traverse of support member 695, annular rings 998 comprised of the plastic material surrounding each aperture 950 are generated at each aperture 145 in lamina 154 of laminate forming structure 240. However, due to the shearing action which occurs between the projecting annular portions of the film and peripherally stationary support member 695 at one or more points across the support member, the excess plastic comprising annular rings 998 is effectively severed, thereby leaving the lowermost surface of the debossed and apertured film 551 substantially coextensive with the innermost surface 465 of tubular forming member 122.

In some product applications, the uniform caliper of the resultant macroscopically expanded, three-dimensional apertured web is particularly desirable. However, in those applications where uniform caliper of the web is less important than the overall softness impression of the web, it has generally been found desirable to utilize a three-dimensional forming structure having an overall thickness which is sufficient to prevent any portion of the macroscopically expanded web from projecting beyond the innermost surface of the tubular forming member. Because no severance of the web occurs in such situations, the harsh feeling typically associated with severed edges is completely avoided.

As has been pointed out earlier herein, support member 695 is preferably supported by means of arcuate projections 696 and 697 which engage arcuate grooves 698 and 699 on wear strips 691 and 692 respectively. The arcuate shape of the projections and mating grooves permits outward and inward movement of support member 695 in a radial direction. To provide uniform support to the innermost surface of tubular forming member 122, yet allow for disturbances occurring during the processing operation, e.g., weld seams in tubular member 122, wear strips 691 and 692 are preferably biased against the innermost surface 465 of tubular forming member 122 by means of forces $F_1$ and $F_2$, respectively. In a particularly preferred embodiment, forces $F_1$ and $F_2$ are equal, and are provided by means of hydraulic or pneumatic cylinders which are controlled by means of a common pressure regulator in order to maintain a constant force between the innermost surface 465 of the tubular forming member 122 and the uppermost surface of support member 695.

As will be appreciated by those skilled in the art, the particular pattern of apertures employed in peripherally stationary support member 695 is non-critical. Rather, it is the relationship between the size, configuration and frequency of the apertures in support member 695 and the size, configuration and frequency of the apertures in tubular forming member 122 which is controlling, i.e., the apertures in tubular forming member 122 must at some point during their traverse of the support member be fully exposed to the fluid pressure differential, yet the support member must provide sufficient support to the innermost surface 465 of tubular forming member 122 that the forming member does not deform excessively during its traverse of the fluid pressure differential zone, e.g., vacuum chamber 662.

Figure 14:
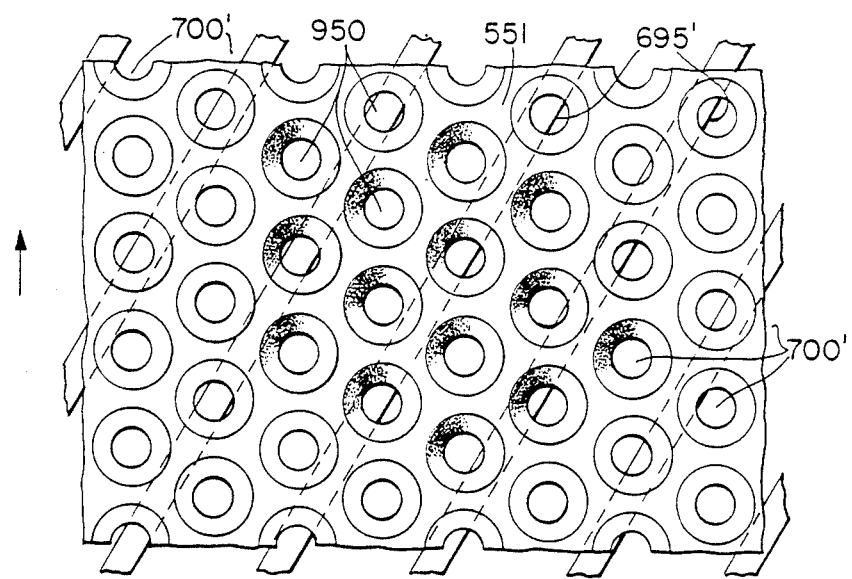
FIG. 14 is an enlarged view generally similar to that of FIG. 13, but showing an alternate embodiment of the peripherally stationary support member.

FIG. 14 discloses an alternative embodiment of the present invention wherein a multiplicity of diagonally oriented apertures 700' are provided in support member 695'. Apertures 700' extend continuously from the leading edge of vacuum chamber 662 to its trailing edge. As a result, support member 695' provides continuous machine direction support to tubular forming member 122 across the vacuum chamber 662. As can be seen from FIG. 14, the relationship between apertures 700' provided in support member 695' and the pattern of apertures 145 in lowermost lamina 154 of tubular forming member 122 is such that every aperture 145 must at some point during its traverse of vacuum chamber 662 be exposed to the fluid pressure differential, i.e., apertures 700' in support member 695' overlap one another in the cross-machine direction so that a continuous, uninterrupted straight line oriented parallel to the machine direction and completely traversing the fluid pressure differential zone cannot be inscribed on the land area defining apertures 700' in the support member 695'. Accordingly, the plastic material comprising planar film 550 is macroscopically expanded into a three-dimensional web 551 having a multiplicity of apertures 950, each corresponding to an aperture 145 in lowermost lamina 154 of tubular forming member 122.

As will be appreciated from the foregoing description, the essence of the present invention is to provide method and apparatus whereby the plastic web to be macroscopically expanded and, if desired, perforated, has its entire surface subjected to a fluid pressure differential at some point during its traverse of a fluid pressure differential zone. This is preferably accomplished by supporting the web on a moving three-dimensional formng structure which is supported in the fluid pressure differential zone by a stationary support member. In a particularly preferred embodiment, these objectives are met by controlling the relationship between the size and pattern of the apertures in the support member and the size and pattern of apertures provided in the forming structure. In particular, the relationship selected must ensure that substantially all of the apertures present in the forming structure are unobstructed by the support member at some point during the forming structure's traverse of the fluid pressure differential zone.

As will be appreciated, providing relative movement between the forming structure per se and the support member utilized to reinforce the forming structure as it is subjected to a fluid pressure differential to uniformly deboss and aperture the web allows much greater flexibility in support structure fabrication and design techniques than was possible in prior art systems where the forming structure had to have sufficient strength to withstand traversing the fluid pressure differential zone without support. For example, lower cost forming structures can be formed utilizing electrodeposition techniques well known in the art in lieu of the more costly laminate fabrication techniques herein disclosed.

In addition, driving each end of the forming structure, as disclosed herein, minimizes torsional stresses normally experienced by the forming structure. Hence a longer useful life is generally obtained.

Similarly, maintaining a constant force between the radially movable but peripherally stationary support member and the innermost surface of the forming structure minimizes the chance of damage to the forming structure in the event unexpected process variations, e.g., seam irregularities, etc., are encountered during the processing operation. In a particularly preferred embodiment, the constant force is continuously regulated at a level high enough to prevent deformation of the forming structure, yet low enough to permit limited deflection of the support member in the event a processing irregularity such as a weld seam is encountered. In this regard, it is, of course, recognized that in an alternate embodiment of the present invention the support member could be rigidly fixed, and a constant force applied to a floating forming structure to provide limited deflection of the forming structure rather than the support member.

It is further recognized, that while the present invention has been illustrated and described in detail relative to the use of substantially rigid tubular forming structures, the present invention may also be practiced to great advantage when flexible forming structures such as screens, belts, patterned masks and the like are employed. Since localized support is provided continuously in both the machine and cross machine directions across the entire fluid pressure differential zone, harmful deformation of the forming structure in the fluid pressure differential zone is essentially eliminated in the practice of the present invention. Accordingly, the only criteria which need be met by the forming structure is that each of the apertures in the forming structure be so sized and spaced relative to the apertures in the stationary support member that they will be fully exposed to the fluid pressure differential at some point during their traverse of the fluid pressure differential zone.

Figure 15:
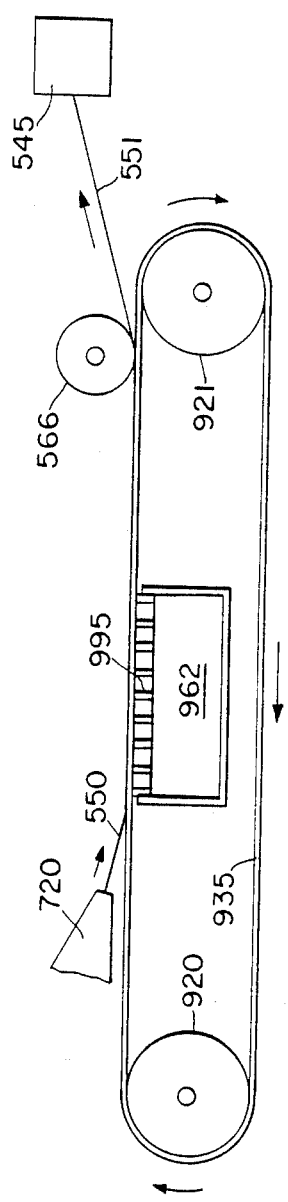
FIG. 15 is a simplified schematic illustration of an alternate apparatus for forming a macroscopically expanded, and if desired, uniformly apertured, three-dimensional plastic web by direct extrusion generally in accordance with the present invention.

A simplified schematic illustration of a process employing a flexible formng structure is schematically disclosed in FIG. 15. In that embodiment, a flexible foraminous forming member 935 operates continuously about a pair of rolls 920, 921. A vacuum chamber 962 is provided intermediate rolls 920, 921. A support member 995 having a multiplicity of apertures which are properly sized and patterned relative to the apertures in flexible forming structure 935 supports the forming structure during its traverse of the vacuum chamber 962. A conventional extruder 720 extrudes a web of plastic material 550 onto the surface of flexible forming structure 935 ahead of the vacuum chamber. A fluid pressure differential is applied by means of vacuum chamber 962 which causes the heated web of plastic material to conform to the three-dimensional pattern present in the flexible forming structure 935. Due to the heat present in the extruded resin, it is normally not necessary to include additional heating means to macroscopically expand the film into a three-dimensional web. Because all of the apertures in the flexible forming structure 935 are subjected to the fluid pressure differential during their traverse of the vacuum chamber, the three-dimensional web 551 is fully debossed and, if desired, apertured in the pattern of the forming structure 935. As with the embodiments shown in FIGS. 9 and 10, the macroscopically expanded three-dimensional web 551 is removed from the forming structure 935 about roll 566 and fed to conventional winding means 545 well known in the art.

From the foregoing description, it will be appreciated that the stationary support member employed in the practice of the present invention may take many and varied forms. For example, the stationary support member could be formed without discrete apertures, provided the material chosen for construction of the support member is sufficiently pervious to fluid flow that it will permit the application of a fluid pressure differential to the apertures present in the forming structure during their traverse of the fluid pressure differential zone. If uniform perforation of the plastic web is also desired, it is of course recognized that the forming structure would have to be of sufficient overall thickness to permit rupture of the web prior to its physically contacting such a fluid pervious support member.

In yet another embodiment of the present invention, a multiplicity of discrete support members could be employed in the fluid pressure differential zone in lieu of a single integral unit of the type generally disclosed herein.

While particular embodiments of the present invention have been illustrated and described, it will be obvious to those skilled in the art that various changes and modifications can be made without departing from the spirit and scope of the invention, and it is intended to cover in the appended claims all such modifications that are within the scope of this invention.

What is claimed is:

1. A method of uniformly debossing a ribbon of substantially planar plastic film as said film moves continuously in the machine direction to impart a fine scale three-dimensional pattern thereto, said method comprising the steps of:

(a) supporting said plastic film on the outermost surface of a three-dimensional forming structure comprising a cylinder moving in the machine direction, said cylinder exhibiting said fine scale three-dimensional pattern, said three-dimensional pattern including a first predetermined pattern of apertures therein; and (b) exposing substantially all portions of said plastic film coinciding with said first pattern of apertures in said cylinder to a fluid pressure differential by transporting said plastic film across a fluid pressure differential zone comprising a peripherally stationary vacuum chamber located inside said cylinder, said cylinder being supported substantially continuously in the machine direction by means of a support member which is also substantially stationary in the machine direction and which contacts the innermost surface of said cylinder to prevent deformation of said cylinder as said cylinder and the film supported thereon traverse said substantially stationary fluid pressure differential zone, said cylinder and said support member being movable relative to one another as measured in a radial direction, whereby a constant force is applied to the innermost surface of said rotating cylinder by moving said support member against the innermost surface of said cylinder to prevent separation therebetween, said substantially stationary support member having a second pattern of apertures therein, said apertures in said second pattern overlapping one another in the cross-machine direction so that a continuous, uninterrupted straight line oriented parallel to the machine direction and completely traversing said fluid pressure differential zone cannot be inscribed on the land area defining said apertures in said support member, said apertures in said substantially stationary support member being so sized and so spaced relative to said first pattern of apertures in said moving cylinder that substantially all of said apertures in said moving cylinder are exposed to the fluid pressure differential existing on the opposite sides of said plastic film in said substantially stationary fluid pressure differential zone at some point during their traverse of said substantially stationary fluid pressure differential zone, whereby said plastic film is uniformly debossed in the undistorted pattern of said three-dimensional forming structure comprising said cylinder.

2. A method of uniformly debossing and aperturing a ribbon of substantially planar plastic film as said film moves continuously in the machine direction to impart a fine scale three-dimensional apertured pattern thereto, said method comprising the steps of:

(a) supporting said plastic film on the outermost surface of a three-dimensional forming structure comprising a cylinder moving in the machine direction, said cylinder exhibiting said fine scale three-dimensional pattern, said three-dimensional pattern including a first predetermined pattern of apertures therein; and (b) exposing substantially all portions of said plastic film coinciding with said first pattern of apertures in said cylinder to a fluid pressure differential by transporting said plastic film across a fluid pressure differential zone comprising a peripherally stationary vacuum chamber located inside said cylinder, said cylinder being supported substantially continuously in the machine direction by means of a support member which is also substantially stationary in the machine direction and which contacts the innermost surface of said cylinder to prevent deformation of said cylinder as said cylinder and the film supported thereon traverse said substantially stationary fluid pressure differential zone, said cylinder and said support member being movable relative to one another as measured in a radial direction, whereby a constant force is applied to the innermost surface of said rotating cylinder by moving said support member against the innermost surface of said cylinder to prevent separation therebetween, said substantially stationary support member having a second pattern of apertures therein, said apertures in said second pattern overlapping one another in the cross-machine direction so that a continuous, uninterrupted straight line oriented parallel to the machine direction and completely traversing said fluid pressure differential zone cannot be inscribed on the land area defining said apertures in said support member, said apertures in said substantially stationary support member being so sized and so spaced relative to said first pattern of apertures in said moving cylinder that substantially all of said apertures in said moving cylinder are exposed to the fluid pressure differential existing on the opposite sides of said plastic film in said substantially stationary fluid pressure differential zone at some point during their traverse of said substantially stationary fluid pressure differential zone, whereby said plastic film is uniformly debossed and apertured in the undistorted pattern of said three-dimensional forming structure comprising said cylinder.

3. A method of continuously forming a uniformly debossed plastic fiml exhibiting a fine scale three-dimensional pattern, said method comprising the steps of:
   (a) continuously extruding a melt of plastic resin in the machine direction to form a substantially planar plastic film;
   (b) supporting said plastic film on the uppermost surface of a three-dimensional forming structure comprising a cylinder moving in the machine direction, said cylinder exhibiting said fine scale three-dimensional pattern, said three-dimensional pattern including a first predetermined pattern of apertures therein; and
   (c) exposing substantially all portions of said plastic film coinciding with said first pattern of apertures in said cylinder to a fluid pressure differential by transporting said plastic film across a fluid pressure differential zone comprising a periphery stationary vacuum chamber located inside said cylinder, said cylinder being supported substantially continuously in the machine direction by means of a support member which is also substantially stationary in the machine direction and which contacts the innermost surface of said cylinder to prevent deformation of said cylinder as said cylinder and the film supported thereon traverse said substantially stationary fluid pessure differential zone, said cylinder and said support member being movable relative to one another as measured in a radial direction, whereby a constant force is applied to the innermost surface of said rotating cylinder by moving said support member against the innermost surface of said cylinder to prevent separation therebetween, said substantially stationary support member having a second pattern of apertures therein, said apertures in said second pattern overlapping one another in the cross-machine direction so that a continuous, uninterrupted straight line oriented parallel to the machine direction and completely traversing said fluid pressure differential zone cannot be inscribed on the land area defining said apertures in said support member, said apertures in said substantially stationary support member being so sized and so spaced relative to said first pattern of apertures in said moving cylinder that substantially all of said apertures in said moving cylinder are exposed to the fluid pressure differential existing on the opposite sides of said plastic film in said substantially stationary fluid pressure differential zone at some point during their traverse of said substantially stationary fluid pressure differential zone, whereby said plastic film is uniformly debossed in the undistorted pattern of said three-dimensional forming structure comprising said cylinder.

4. A method of continuously forming a uniformly debossed and apertured plastic film exhibiting a fine scale three-dimensional pattern, said method comprising the steps of:
   (a) continuously extruding a melt of plastic resin in the machine direction to form a substantially planar plastic film;
   (b) supporting said plastic film on the uppermost surface of a three-dimensional forming structure comprising a cylinder moving in the machine direction, said cylinder exhibiting said fine scale three-dimensional pattern, said three-dimensional pattern including a first predetermined pattern of apertures therein; and
   (c) exposing substantially all portion of said plastic film coinciding with said first pattern of apertures in said cylinder to a fluid pressure differential by transporting said plastic film across a fluid pressure differential zone comprising a peripherally stationary vacuum chamber located inside said cylinder, said cylinder being supported substantially continuously in the machine direction by means of a support member which is also substantially stationary in the machine direction and which contacts the innermost surface of said cylinder to prevent deformation of said cylinder as said cylinder and the film supported thereon traverse said substantially stationary fluid pressure differential zone, said cylinder and said support member being movable relative to one another as measured in a radial direction, whereby a constant force is applied to the innermost surface of said rotating cylinder by moving said support member against the innermost surface of said cylinder to prevent separation therebetween, said substantially stationary support member having a second pattern of apertures therein, said apertures in said second pattern overlapping one another in the cross-machine direction so that a continuous, uninterrupted straight line oriented parallel to the machine direction and completely traversing said fluid pressure differential zone cannot be inscribed on the land area defining said apertures in said support member, said apertures in said substantially stationary support member being so sized and so spaced relative to said first pattern of apertures in said moving cylinder that substantially all of said apertures in said moving cylinder are exposed to the fluid pressure differential existing on the opposite sides of said plastic film in said substantially stationary fluid pressure differential zone at some point during their traverse of said substantially stationary fluid pressure differential zone, whereby said plastic film is uniformly debossed and apertured in the undistorted pattern of said three-dimensional forming structure comprising said cylinder.

* * * * *

UNITED STATES PATENT AND TRADEMARK OFFICE
CERTIFICATE OF CORRECTION

PATENT NO. : 4,741,877

DATED : May 3, 1988

INVENTOR(S) : William I. Mullane

It is certified that error appears in the above-identified patent and that said Letters Patent is hereby corrected as shown below:

Column 1, line 60, "illustrating" should read -- illustrated --.

Column 2, line 34, "2,021,497A" should read -- 2,021,479A --.

Column 3, line 44, "become" should read -- becomes --.

Column 4, line 11, "and" should read -- said --.

Column 5, line 8, "structure" should read -- structures --.

Column 6, line 61, "refer" should read -- refers --.

Column 8, line 21, "apertures" should read -- apertured --.

Column 9, line 21, "apertures" should read -- apertured --.

Column 13, line 1, "54" should read -- 154 --.

Column 13, line 27, "structure" should read -- structures --.

Column 14, line 40, after "683" insert --, --.

Column 17, line 49, "formng" should read -- forming --.

Column 18, line 46, "formng" should read -- forming --.

Column 21, Claim 3, Line 8, "fiml" should read -- film --.

UNITED STATES PATENT AND TRADEMARK OFFICE
CERTIFICATE OF CORRECTION

PATENT NO. : 4,741,877

DATED : May 3, 1988

INVENTOR(S) : William I. Mullane

It is certified that error appears in the above-identified patent and that said Letters Patent is hereby corrected as shown below:

Column 21, Claim 3, line 24, "periphery" should read -- peripherally --.

Column 22, Claim 4, line 17, "portion" should read -- portions --.

Signed and Sealed this

Thirtieth Day of August, 1988

Attest:

DONALD J. QUIGG

*Attesting Officer*  *Commissioner of Patents and Trademarks*